United States Patent [19]

Eibl et al.

[11] 4,098,660
[45] Jul. 4, 1978

[54] METHOD OF PURIFYING WATER

[75] Inventors: Volker Eibl; August Ries, both of Munich, Germany

[73] Assignee: Sachs Systemtechnik GmbH, Schweinfurt am Main, Germany

[21] Appl. No.: 810,867

[22] Filed: Jun. 28, 1977

Related U.S. Application Data

[63] Continuation-in-part of Ser. No. 619,696, Oct. 6, 1975, which is a continuation-in-part of Ser. No. 473,389, May 28, 1974, Pat. No. 3,923,632.

[30] Foreign Application Priority Data

Jun. 9, 1973 [DE] Fed. Rep. of Germany ....... 2329628

[51] Int. Cl.² ........................... C02B 1/82; C02B 3/10
[52] U.S. Cl. ..................................... 204/151; 204/149
[58] Field of Search ................... 204/149, 151, 180 P, 204/130; 426/321

[56] References Cited

U.S. PATENT DOCUMENTS

| 2,046,467 | 7/1936 | Krause | 204/149 |
| 2,882,210 | 4/1959 | Jenks | 204/151 |

FOREIGN PATENT DOCUMENTS

| 428,764 | 5/1935 | United Kingdom | 204/149 |
| 514,089 | 1/1940 | United Kingdom | 204/149 |

Primary Examiner—Arthur C. Prescott
Attorney, Agent, or Firm—Hans Berman

[57] ABSTRACT

Water contaminated with pathogenic microorganisms is passed over a silver anode of an electrolyte cell in a layer 1 to 4 mm thick. The anode surface and the rate of water flow through the cell are related according to the equation $F \geqq c \times V$, wherein $F$ is the anode surface area in cm², $V$ is the water flow rate in cm³/second and $c$ is a constant of the dimension sec/cm, with a value of 2 to 5. The density of the current in relation to the area of the anode surface is between 1.5 and 3.0 mA/cm² and the voltage is such that active oxygen is generated at the anode. The effluent from the cell is safe to drink.

10 Claims, 1 Drawing Figure

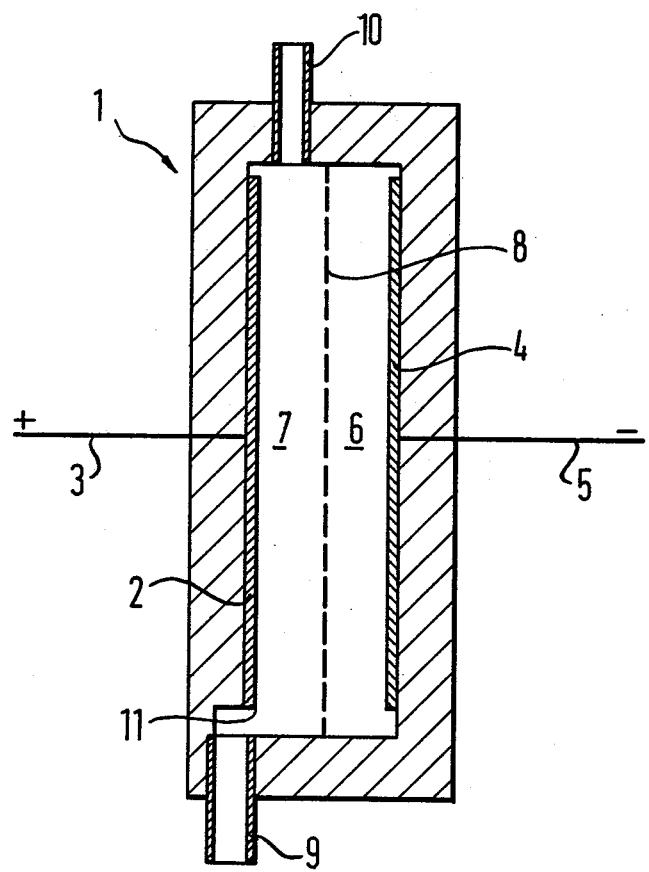

METHOD OF PURIFYING WATER

This is a continuation-in-part of our copending application Ser. No. 619,696, filed on Oct. 6, 1975, which itself is a continuation-in-part of application Ser. No. 473,389, filed May 28, 1974, now U.S. Pat. No. 3,923,632.

The present invention relates to improvements in a method of purifying water contaminated with microorganisms and having a specific resistance in the range of about $0.5 \times 10^3$ ohm $\times$ cm to about $6.6 \times 10^3$ ohm $\times$ cm. The method is performed in an electrolytic cell including a silver-containing anode, and the water to be purified flows substantially parallel to the anode surface. The anode may be made of a material containing metallic silver or of substantially pure (99%) silver.

The method of this invention aims at avoiding disinfective additives whose exact amounts are often difficult to determine and which frequently limit the use of the water. In the method of the invention, the water is not only to be disinfected, but also decontaminated and detoxicated, bacteriological contaminants being converted into non-toxic compounds.

The above and other objects are accomplished according to the present invention by passage of the water through an electrolytic cell over the surface of an anode of conductive silver-containing material in a stream having a thickness $d$ of about 1 to about 4 mm, preferably not more than 2 mm, as measured at right angles to the anode surface. The anode surface and the rate of the water flow through the space are related according to the equation $F \geqq c \times \dot{V}$, wherein $F$ is the area of the anode surface in cm$^2$, $\dot{V}$ is the flow rate in cm$^3$/second and $c$ is a factor of the dimension sec/cm, $c$ being at least 2 when $d = 1$ mm, at least 3 when $d = 2$ mm, and at least 5 when $d = 4$ mm. For intermediate values of $d$, the minimum magnitude of $c$ is calculated by linear interpolation between the afore-mentioned values of $d$, whereby the numerical value of $c$, is sec/cm, is at least equal to the numerical value of $d$, in millimeter, plus one. The electric current passing through the water from a cathode to the anode must provide an anode current density of about 1.5 mA/cm$^2$ and 3.0 mA/cm$^2$, and the voltage applied to the cell is chosen to generate axtive oxygen and silver ions at the anode.

The above-indicated dimensions and relationships have been determined experimentally. It has been found that it is necessary to confine the stream of water in a flow section of 1 to 4 mm from the anode in order to subject all the water simultaneously to anodic oxidation and to enrichment with silver ions. While the enrichment with silver ions would be obtained also with a wider spacing, anodic oxidation can be obtained only if the distance between the electrodes does not exceed 4 mm. On the other hand, if the water layer is thinner than 1 mm, and the applied voltage sufficient to generate active oxygen at the anode, more silver ions would enter the water than is practical. Silver ion enrichment and anodic oxidation synergistically produce a degree of purification not obtainable otherwise.

Anodic oxidation of microorganisms requires the generating of active oxygen at the anode to oxidize organic matter in the adjacent water. When anodic oxidation is combined with silver ion enrichment, the dwell time of the water in the electrolytic cell can be reduced to commercially useful periods and still achieve complete sterilization.

The constant $c$ should be limited to the indicated minimum values to hold the size of the apparatus within desirable dimensions and to avoid long periods of treatment. The terminal voltage may be between about 1.8 volts and about 12 volts if the space within the electrolytic cell is bounded by the electrode surfaces. The voltage may be higher than 12 volts, if the space is bounded by the anode surface and a diaphragm and the distance between the electrode surfaces is greater than 4 mm.

Other objects, features and advantages of the present invention will become apparent from the following description of apparatus for performing the method, taken in conjunction with the single FIGURE of the accompanying drawing which shows the apparatus in elevational section.

The container of an electrolytic cell encloses an anode 2 and a cathode 4. The space between the anode and the cathode surfaces is divided into anode and cathode compartments 7, 6 by a semi-permeable membrane or diaphragm 8. Contaminated water is admitted to the anode compartment through an inlet 9 and purified water is withdrawn from the same compartment at an outlet 10. The water flows from the inlet to the outlet in a direction substantially parallel to the anode and diaphragm surfaces. The water entering the cell 1 through the inlet 9 is directed first against an edge 11 of the anode 2 to create a turbulent flow within the anode compartment 7. Lead 3 of a direct-current source (not shown) is connected to the anode and lead 5 to the cathode. The diaphragm 8 is permeable to anions only. However, the diaphragm may be omitted so that thickness of the stream of water at right angles to the anode surface is defined by the distance of the exposed, parallel electrode surfaces.

The apparatus is operated as follows:

The water to be disinfected flows through the water inlet 9 into the anode compartment 7 and is subjected there to the current flowing between the anode 2 and the cathode 4. The microorganisms within the water are decomposed or at least inactivated by anodic oxidation.

An asbestos sheet may be used as a diaphragm, but particularly advantageous results have been obtained with a material only permeable to anions. However, the diaphragm may be omitted entirely if other conditions are suitably controlled.

The following examples further illustrate this invention.

EXAMPLE 1

A rectangular cell of the generally illustrated type had electrode surfaces $6 \times 6$ cm spaced 2 mm apart without interposed diaphragm. Thus, the flow section of the water stream between the anode and cathode was $6 \times 0.2$ cm$^2$ and the volume of water exposed to the current at any given time was 7.2 cm$^3$.

The anode consisted of silver, 99% pure, while the cathode consisted of chromium-nickel-molybdenum steel (18% Cr, 11% Ni, 2% Mo).

Munich tap water having a specific resistance of 2.08 $\times 10^3$ ohm · cm and a pH of 7.5 was contaminated with $1.887 \times 10^7$ coliform microorganisms per milliliter. The rate of water flow through the cell was controlled at 6 cm$^3$/second for an average dwell time of 1.2 seconds.

A potential of 2.6 V was applied to the electrodes, and the formation of active oxygen was noted at the anode. The current density was 2.7 mA per cm$^2$ of anode surface.

A specimen of the cell effluent was diluted stepwise with sterile water until the diluted liquid contained one part of volume of effluent per 10,000 parts. A sterilized nutrient medium was inoculated with the diluted liquid and incubated for three days at 37° C. No microorganisms could thereafter be detected on the culture medium.

In a second test, a 200 ml batch of undiluted effluent was filtered through a sterile sheet of cellulosic material known to retain coliform microorganisms while retaining only a negligible amount of silver ions. The face of the sheet receiving the treated water was rinsed with sterile water, the washings were filtered through another sheet of the same material, and the second filter sheet was then placed in a Petri dish containing a sterilized nutrient medium. The dish was incubated for 3 days at 37° C, and was thereafter found not to carry microorganisms.

EXAMPLE 2

The electrolytic treatment of Example 1 was repeated under otherwise identical conditions with a cell whose silver anode was replaced by a stainless steel anode, and the tap water subjected to electrolytic treatment contained initially $4 \times 10^5$ coliform microorganisms per milliliter.

A batch of sterile water was subjected to electrolytic treatment in the cell described in Example 1 until its silver ion content was twice that of the water treated in Example 1. Equal amounts of the electrolyzed contaminated water and of the electrolyzed, silver-bearing, but sterile water were mixed. After 2 minutes batches of the mixtures were subjected to the two bacteriological tests described in Example 1.

The number of colonies counted after inoculation of the diluted medium indicated that the microorganism content of the water electrolyzed between inert electrodes was still $5.5 \times 10^3$ microorganisms per milliliter.

The filter sheet employed in the second test caused a dense growth of filamentous microorganisms over practically the entire exposed surface of the culture medium in the Petri dish.

What is claimed is:

1. A method of purifying water contaminated with microorganisms and having a specific resistance of approximately $0.5 \times 10^3$ ohm · cm to approximately $6.6 \times 10^3$ ohm · cm which comprises:
    (a) passing a stream of said water over a surface of conductive, silver-containing material,
        (1) the thickness of said stream at right angles to said surface being not greater than 4 millimeters; and
    (b) passing direct electric current between said surface as an anode and said contaminated water at a density of 1.5 to 3.0 mA per square centimeter of said surface,
        (1) the area F of said surface in square centimeters and the flow rate $\dot{V}$ of said stream in cm$^3$/second satisfying the relationship $F \geq c \times \dot{V}$, wherein c is a factor whose numerical value, in sec/cm, is at least equal to the numerical value of said thickness, in millimeters, plus one.

2. A method as set forth in claim 1, wherein said thickness is at least 1 mm.

3. A method as set forth in claim 2, wherein said direct electric current is generated by establishing a potential between said surface and said water sufficient to generate active oxygen at said surface.

4. A method as set forth in claim 2, wherein said thickness is not greater than 2 mm.

5. A method as set forth in claim 2, wherein the surface of said material contains at least 99% silver.

6. A method as set forth in claim 2, wherein said current is passed to said contaminated water from a surface of a cathode bounding said stream in a direction perpendicular to said surface of silver-containing material.

7. A method as set forth in claim 2, wherein said density is approximately 2.7 mA per square centimeter of said surface.

8. A method as set forth in claim 2, wherein turbulence is generated in said stream, said surface being substantially planar.

9. A method as set forth in claim 2, wherein said current is passed to said contaminated water from a cathode through a selectively permeable diaphragm bounding said stream in a direction perpendicular to said surface of silver-containing material.

10. A method as set forth in claim 1, wherein said numerical value of said factor $c$ is not substantially greater than said numerical value of said thickness, in millimeters, plus one.

* * * * *